United States Patent [19]

Frey

[11] Patent Number: 5,167,954

[45] Date of Patent: Dec. 1, 1992

[54] HAIR LOTION CONTAINING CARDOMOM AND USE THEREOF

[76] Inventor: Helga Frey, Viale P. Orlando, 7 - 00122 Lido di Ostia, Roma, Italy

[21] Appl. No.: 429,419

[22] Filed: Oct. 31, 1989

Related U.S. Application Data

[63] Continuation of PCT/IT89/00014, Mar. 8, 1989, published as WO89/09047, Oct. 5, 1989.

[30] Foreign Application Priority Data

Mar. 28, 1988 [IT] Italy .................. 47782 A/88

[51] Int. Cl.⁵ .................. A61K 7/06; A61K 35/78
[52] U.S. Cl. .................. 424/74; 424/70; 424/195.1

[58] Field of Search .................. 424/195.1, 74, 70

[56] References Cited

U.S. PATENT DOCUMENTS 4,626,427 12/1986 Wienecke et al. .................. 424/35

Primary Examiner—Michael L. Shippen
Assistant Examiner—Vera C. Clarke
Attorney, Agent, or Firm—Beveridge, DeGrandi & Weilacher

[57] ABSTRACT

A composition, method for producing and method of use of a hair lotion is disclosed. The hair lotion is based on an ethyl alcohol extract of cardamom and distilled water. The hair lotion may optionally include camomile extract and/or orange flower water. The lotion has been shown to be effective in reinforcing and invigorating hair.

18 Claims, No Drawings

HAIR LOTION CONTAINING CARDOMOM AND USE THEREOF

This is a continuation of PCT/IT89/00014 application filed Mar. 8, 1989, now WO 89/09047.

The present invention consists of a hair lotion composition, the production process and the use thereof.

Personal grooming has assumed great importance in our societies and the market offers a wide choice of products for these purposes. Particular importance is hair care in consideration of the fact that in the last years an increasing number of persons have been suffering from premature hair thinning or even partial or complete loss of hair on some areas of the scalp or even on the entire surface thereof. In order to alleviate this problem, considered very grave by some for aesthetic reasons, various treatments have been developed, such as hair transplants or artificial hair implants and local treatments with various substances. The latter usually consist, whenever applicable (i.e. as long as the hair bulbs, even though showing reduced growth capacity, are still alive), of local applications with substances aimed at restimulating the vitality of the hair bulbs and to remove eventual excess oiliness of the scalp. Innumerous findings, in line with ongoing technology, utilize this principle and, from time to time, according to the specific hair problem addressed, have given rise to results which were not always entirely satisfactory.

As a great surprise comes the discovery that a hair lotion based on the alcoholic extract of cardamom shows particularly effective results in the sense that it helps to reinforce and improve the hair quality.

Therefore, object of this invention is a composition of a hair lotion consisting of:

a) 13-17% in volume of alcoholic extract of cardamom, obtained by macerating 13-17 gr. cardamom powder, obtained by grinding dried fruits of *Elettaria Cardamomum*, for each 100 cc of ethyl alcohol at approximately 70% for about 7 days, and b) 87-83% in volume of distilled water.

Cardamom, which is utilized in the composition of this invention, is a plant which grows spontaneously and abundantly in the homonymous mountains located in the southern part of the Indian East-coast. The Latin name of the plant is "*Elettaria Cardamomum*" of which numerous varieties are known, the white variety being the most suitable for the preparation of the hair lotion according to this invention, as it does not alter the color of the hair when applied.

Furthermore it has been proven to be advantageous to use in the composition according to the present invention also camomile extracts due to its soothing and disinfecting properties, as well as orange-blossom water which enhances the fragrance of said hair lotion.

A further object of the present invention is the process for the production of the hair lotion composition according to the present invention comprising the following operations:

a) preparing an alcoholic extract of cardamom by macerating 14-16 gr of powdered cardamom, obtained by grinding dried fruits of *Elettaria cardamomum* for each 100 cc of ethyl alcohol at approximately 70% for about 7 days, b) filtering the solution to separate the solids and adding further ethyl alcohol at approximately 70% until reaching again the volume of 100 cc, and c) diluting an appropriate quantity of the extract, obtained as described above, in distilled water so as to obtain a solution from 13 to 17% in volume.

Further object of the present invention is the use of the hair lotion in the treatment for reinforcing and invigorating of the hair.

The hair lotion composition according to present invention, is used as any hair lotion, i.e. by applying the same to the scalp with a light massage as often as the individual case may require. The hair lotion has a slightly milky appearance, a pleasant scent, is non-oily, does not alter the hair color and, above all, is nontoxic.

Following are some of the most suitable formulae for the composition of the hair lotion according to the present invention:

| Formula 1 | |
|---|---|
| Alcoholic cardamom extract | 15 cc |
| Distilled water | 85 cc |
| Formula 2 | |
| Alcoholic cardamom extract | 15 cc |
| Camomile extract | 5 cc |
| Distilled water | 80 cc |
| Formula 3 | |
| Alcoholic cardamom extract | 15 cc |
| Orange-flower water | 25 cc |
| Distilled water | 60 cc |
| Formula 4 | |
| Alcoholic cardamom extract | 15 cc |
| Camomile extract | 5 cc |
| Orange-flower water | 20 cc |
| Distilled water | 60 cc |

Both camomile extract and the orange-flower water are well-known in the preparation of hair lotions; therefore, it is unnecessary to give a detailed description of their respective production.

The composition of the hair lotion according to the present invention has been tested for a period of approximately six (6) months by fifty (50) subjects of either sex between 15 and 65 years old suffering from light to severe hair loss. The hair lotion was applied from once a day to 2 or 3 times, according to need, followed by a light massage of the scalp.

It is obvious that to the composition of the hair lotion according to the present invention various additives and excipients known in the production technology of this sector may be added, such as conservatives, essences, emollients, disinfectants, and similar substances; therefore, without going out of the limits of the present invention, compositions of the hair lotion formulated in any such manner fall equally within the range of protection afforded by this invention.

I claim:

1. A hair lotion composition comprising:
   a) 13-17% in volume of an alcoholic extract of cardamom, said extract obtained by macerating 13-17 grams of powdered cardamom for each 100 cc of an about 70% ethyl alcohol solution for about 7 days; said powdered cardamom, obtained by grinding the dried fruits of *Elettaria cardamomum*, and
   b) 87-83% in volume of distilled water.

2. A hair lotion composition according to claim 1, wherein the above mentioned dried fruits belong to the white variety of *Elettaria cardamomum*.

3. A process for the production of a hair lotion composition which comprises:
   a) preparing an alcoholic cardamom extract by macerating 13 to 17 grams of powdered cardamom for each 100 cc of an about 70% ethyl alcohol solution for about 7 days, said powdered cardamom obtained by grinding the corresponding amount of dried fruits of *Elettaria cardamomum*, filtering a solution obtained by maceration to remove solids and adding a sufficient amount of approximately 70% ethyl alcohol until the volume again becomes 100 cc for each initial 100 cc of ethyl alcohol solution, and b) diluting an appropriate amount of the extract obtained as described above in distilled water until obtaining a solution with about 13-17% extract in volume.

4. A hair lotion composition, comprising:
a) about 13-17% by volume of an ethyl alcohol extract of cardamom based on the final lotion volume; and
b) distilled water.

5. The hair lotion composition according to claim 4, further comprising about 5% by volume of a camomile extract, based on the final lotion volume.

6. The hair lotion composition according to claim 4, further comprising about 20-30% by volume of an orange flower water, based on the final lotion volume.

7. The hair lotion composition according to claim 5, further comprising about 20-30% by volume of an orange flower water based on the final lotion volume.

8. The hair lotion composition according to claim 4, wherein the hair lotion further includes at least one of the additional ingredients chosen from the group consisting of: conservatives, essences, emollients and disinfectants.

9. A process for preparing a hair lotion composition comprising:

a) preparing an alcoholic extract of cardamom by macerating powdered cardamom with an ethyl alcohol solution;
b) filtering the macerated solution to seperate the solids;
c) adding a sufficient quantity of ethyl alcohol to return to the initial volume thereby providing the extract; and
d) diluting a quantity of the extract with distilled water to obtain a 13-17% by volume solution of the extract.

10. The process according to claim 9, wherein the macerating takes place for about seven days.

11. The process according to claim 9, wherein the ethyl alcohol is an approximately 70% ethyl alcohol solution.

12. The process according to claim 9, further including the step of adding a camomile extract to the cardamom extract.

13. The process according to claim 12, wherein about 5% by volume of camomile extract is added based on the final volume of the hair lotion.

14. The process according to claim 12, further including the step of adding orange flower water to the cardamom extract.

15. The process according to claim 14, wherein 20-30% by volume of orange flower water is added based on the final volume of the hair lotion.

16. The process according to claim 9, further including the step of adding orange flower water to the cardamom extract.

17. The process according to claim 16, wherein 20-30% by volume of orange flower water is added based on the final volume of the hair lotion.

18. A method for reinforcing and invigorating hair with the hair lotion composition according to claim 14 comprising massaging the hair lotion into the scalp at least once a day.

* * * * *